(12) United States Patent
Gaspar (10) Patent No.: US 6,772,461 B2
(45) Date of Patent: Aug. 10, 2004

(54) PORTABLE TRAUMA RADIOGRAPHY/ PATIENT CARE SYSTEM

(76) Inventor: David Gaspar, 17 Wintermeadow St., Barre, VT (US) 05641

(*) Notice: Subject to any disclaimer, the term of this patent is extended or adjusted under 35 U.S.C. 154(b) by 0 days.

(21) Appl. No.: 09/865,168

(22) Filed: May 24, 2001

(65) Prior Publication Data

US 2001/0044967 A1 Nov. 29, 2001

Related U.S. Application Data

(60) Provisional application No. 60/206,692, filed on May 24, 2000.

(51) Int. Cl.[7] .............................................. A47B 7/00
(52) U.S. Cl. ................................. 5/632; 5/605; 5/601
(58) Field of Search ........................... 5/632, 625, 601, 5/621, 623, 624

(56) References Cited

U.S. PATENT DOCUMENTS

| | | | | |
|---|---|---|---|---|
| 3,215,834 A | * | 11/1965 | Taymen | 378/174 |
| 3,779,211 A | * | 12/1973 | Etes | 119/753 |
| 3,826,922 A | * | 7/1974 | Ingles | 378/181 |
| 3,840,221 A | * | 10/1974 | Hogan | 5/601 |
| 4,947,418 A | * | 8/1990 | Barr et al. | 378/177 |
| 5,016,268 A | * | 5/1991 | Lotman | 378/177 |
| 5,255,303 A | * | 10/1993 | DiMaio et al. | 378/177 |
| 5,675,854 A | * | 10/1997 | Zibelin | 5/695 |
| 5,764,724 A | * | 6/1998 | Ohlson | 378/177 |
| 6,266,831 B1 | * | 7/2001 | Heimbrock | 5/601 |

* cited by examiner

*Primary Examiner*—Teri Pham Luu
*Assistant Examiner*—Fredrick Conley
(74) *Attorney, Agent, or Firm*—James Marc Leas (57) ABSTRACT

A system for supporting a patient on a removable patient support unit, such as a backboard, includes a platform having spaced elements for supporting the removable patient support unit. The patient support unit is elevated above the platform and there is an unimpeded region between the platform and the patient support unit to facilitate placing x-ray film cassettes under the patient. The x-ray film cassettes can be placed and adjusted without disturbing the patient. The platform has features to hold x-ray film cassettes in a vertical position, catch and hold blood, support the backboard at an angle, and provide containers for sharp instruments. The system also includes arm boards for constraining the patient. A mattress covered bed can also be used with the platform.

41 Claims, 7 Drawing Sheets

PORTABLE TRAUMA RADIOGRAPHY/PATIENT CARE SYSTEM this application claims the benefit of Provisional application No. 60/206,692 filed May 24, 2000.

FIELD OF THE INVENTION

This invention generally relates to trauma patient care. More particularly, it relates to a system for supporting a trauma care patient. Even more particularly, it relates to a system for supporting a trauma care patient during a procedure such as X-ray.

BACKGROUND OF THE INVENTION

Emergency care of trauma victims can be a high tension and potentially dangerous situation for both the patient and the care giver. Providing expedient, safe and accurate care is made difficult by factors associated with trauma, such as massive amounts of blood that could be on the stretcher and floor. In addition there are risks associated with needles used for treatment. And there are further difficulties with safely turning and supporting a patient that is aspirating while restrained on a backboard. Additional risk arises from a potentially violent patient. All these are compounded when the facility has few staff members available for such a patient or for a heavy set patient.

Portable radiography plays a valuable role in the diagnosis and selection of treatment for trauma victims. However, the need for quality and expediently produced radiographs has not always been fulfilled because of the time and the difficulties posed by handling trauma patients and the time and staff required to set up for x-rays.

Typically, trauma patients are restrained on a backboard or a stretcher, and it is difficult and time consuming to properly position x-ray cassettes under or adjacent a patient on a backboard or stretcher. Sometimes patients must be repeatedly moved around to properly position or reposition the x-ray film cassettes. This not only takes critical time but the movements needed can require several staff members and can cause delay or further problems for the patient.

In addition, if the x-ray film cassette comes in contact with blood it must be completely cleaned and disinfected before it can be developed, taking additional time. There are risks to staff as well from physical contact with the patient to adjust his or her position since contact with the patient's blood may subject the worker to serious illness.

In addition certain x-rays, such as cross-table laterals, can be extremely difficult to take with trauma patients who must be restrained in a fixed position. In most cases, a cassette is propped up against the side rail of the stretcher using tape. However, sometimes the side rail cannot be raised because the patient's injured arm is in the way and cannot be moved. While alternate schemes may then be devised, the resulting x-rays are often degraded despite the great need for high quality results for seriously injured trauma victims. This is especially a problem where multiple x-rays of multiple body parts are needed. If the patient must be moved around or if a long time appears to be necessary for setting up or taking the x-rays, then this critical diagnostic technique may not be used at all.

Thus, a better system for supporting a trauma care patient is needed. This system is particularly needed for supporting a trauma care patient during procedures such as x-ray, and this improved system is provided by the following invention.

SUMMARY OF THE INVENTION

It is therefore an object of the present invention to provide a platform for supporting a patient that allows rapidly taking x-rays of any part of a patient's body without moving the patient.

It is a further object of the present invention that the platform has a facility for collecting bodily fluids, such as blood, dripping from a trauma victim;

It is a further object of the present invention that the platform also has a facility for supporting an x ray cassette vertically or horizontally;

It is a further object of the present invention that the facility for supporting an x ray cassette vertically or horizontally allows it to be moved without moving the patient;

It is a further object of the present invention to provide a convenient way to support a patient turned at an angle;

It is a further object of the present invention to provide a convenient way to safely dispose of needles adjacent the platform;

It is a further object of the present invention to provide a way to constrain the arms of a patient;

It is a feature of the present invention that the platform has spaced elements for supporting a removable patient support unit elevated above the platform to provide an unimpeded region between the platform and the patient support unit;

It is a feature of the present invention that the platform has troughs for collecting bodily fluids;

It is a feature of the present invention that the platform also has a central support area for supporting an x ray cassette in a horizontal position;

It is a feature of the present invention to provide a moveable device for supporting an x ray cassette in a vertical position; and It is an advantage of the present invention that the platform allows a technologist to speedily take x-rays of or perform other procedures on a trauma patient without moving the patient.

These and other objects, features, and advantages of the invention are accomplished by a system for supporting a patient, comprising a platform having having an upper surface. The upper surface has spaced elements for supporting a removable patient support unit elevated above the upper surface. An unimpeded region is between the upper surface and the removable patient support unit.

Another aspect of the invention is a system for supporting a patient, comprising a platform for supporting the patient support unit. The platform has a plurality of structures for holding a removable X ray cassette holder.

Another aspect of the invention is a system for supporting a patient, comprising a platform for supporting the patient support unit, the platform having a trough for collecting bodily fluids.

Another aspect of the invention is a system for supporting a patient, comprising a platform for supporting a patient support unit, the platform having a structure for holding a removable container.

Another aspect of the invention is a system for supporting a patient, comprising a platform for supporting a patient support unit, wherein said platform comprises spaced elements for supporting the patient support unit in a fixed position.

BRIEF DESCRIPTION OF THE DRAWINGS

The foregoing and other objects, features, and advantages of the invention will be apparent from the following detailed description of the invention, as illustrated in the accompanying drawings, in which:

FIG. 4b is a bottom view of the mattress covered bed of FIG. 4a; and FIGS. 4c and 4d are cross sectional views of the mattress covered bed of FIG. 4a.

DETAILED DESCRIPTION OF THE INVENTION

The present inventor recognized several problems with traditional trauma patient care. He further recognized the importance of x-rays in characterizing the extent of injury and the fact that present facilities are not able to provide those x-rays quickly and are not able to provide those x-rays without moving the trauma patient. Further, he recognized that there were inadequate facilities for properly holding x-ray film cassettes, for accommodating sharp instrument disposal, and for catching body fluids, such as blood from the patient.

To solve these problems the present inventor designed a platform system that allows substantially improved patient care. One improvement facilitates taking x-rays. The trauma patient on a standard patient support unit, such as a backboard, is placed on a platform having spaced elements, such as blocks or ribs. The spaced elements hold the patient support unit above the platform leaving an unimpeded region between the platform and the patient support unit. X-ray cassettes can be quickly inserted and adjusted in this region between the removable backboard and the platform permitting x-rays to be quickly taken of any body region without moving the patient. X-ray cassettes can hold radiation sensitive media sensitive to x-ray, such as x-ray film or a digital imager, as is well known in the art. The platform has other features, as more fully described herein below to hold x-ray cassettes at various other angles and positions, to catch blood, to restrain a violent patient in a fixed position, to permit tilting of the patient on his or her side while the patient is still on the back board, and to hold containers for needles and other sharp instruments.

Figures 1A, 1B, 1C:
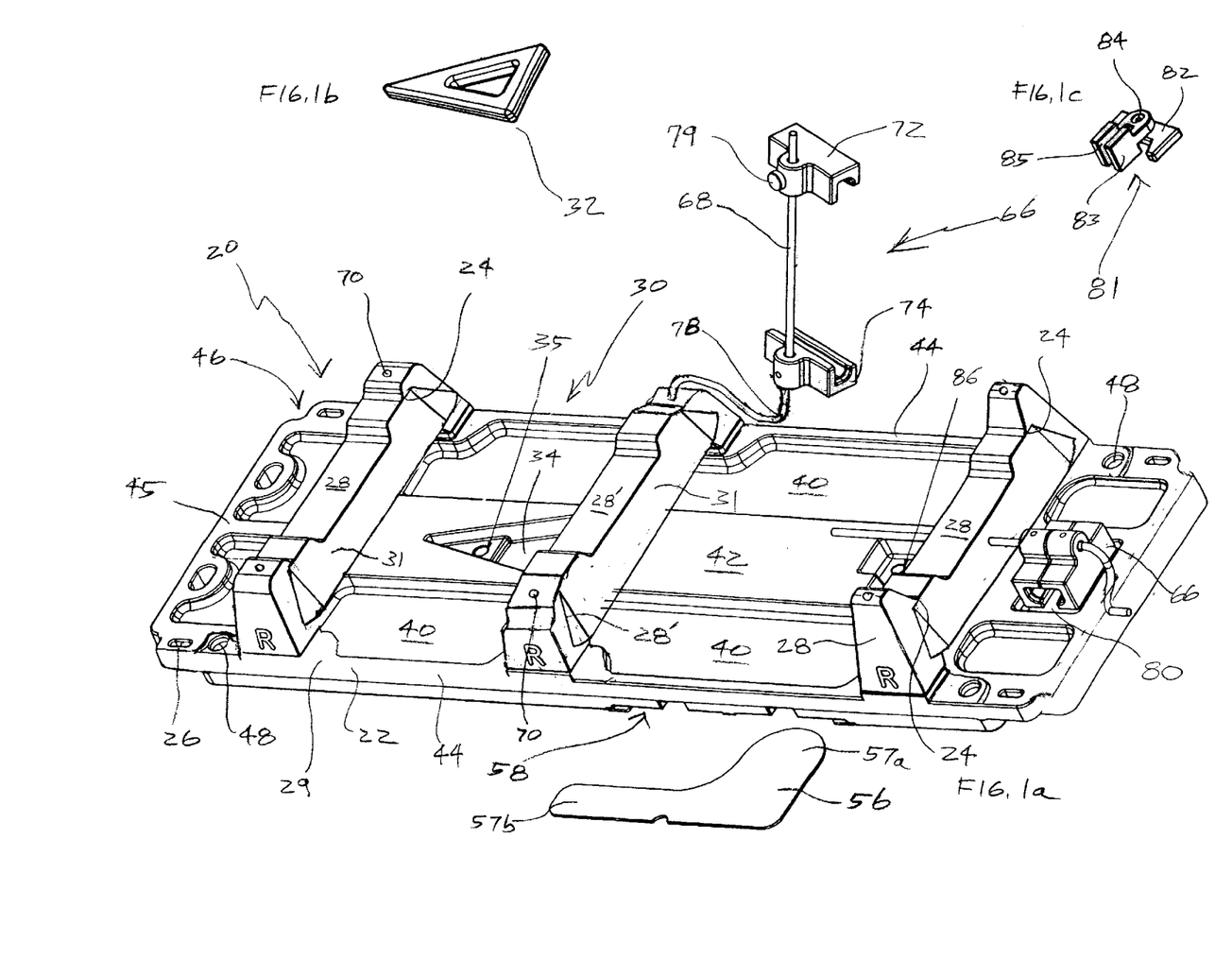
FIG. 1a is a perspective view of the platform, arm units, angle supporter, and x-ray cassette holders of the present invention.
FIG. 1b is a perspective view of the angle device used to support the platform at an angle.
FIG. 1c is a perspective view of a small x-ray film cassette holder used in conjunction with the platform.

Portable trauma radiography patient care system 20 includes platform 22, as shown in FIG. 1a. A standard removable patient support unit (not shown) such as a standard backboard, with the patient (not shown), is placed on platform 22, fitting into contours 24 of platform 22 for improved stability.

Platform 22 may be placed on a standard stretcher (not shown), and can be connected to the stretcher with straps (not shown) provided through slots 26. Velcro can be used for the straps to firmly connect platform 22 to the stretcher.

Spaced elements 28 are located on upper surface 29 platform 22 while openings 30 are between spaced elements 28. Spaced elements 28 support the backboard supporting the patient while openings 30 allow x-ray cassettes (not shown) to be placed under any part of the patient. Spaced elements 28 can be configured as blocks or ribs, as shown in FIG. 1a, and bridge across openings 30. Because the backboard is placed on spaced elements 28, and not directly on a wide base or on a stretcher, a film cassette positioned under the patient always remains completely visible and accessible and can easily be repositioned. Film cassettes can be located anywhere between or under spaced elements 28, so x-rays can be taken of any part of a patient's body. Spaced elements 28 are attached to platform 22 or they are integrally formed as part of platform 22. Sidewalls 31 of spaced elements 28 curve outward, as shown in FIG. 1a. Providing sidewalls 31 of spaced elements 28 at a non-perpendicular angle to upper surface 29 of platform 22 prevents sidewalls 31 from appearing as lines on x-rays. An "R" is molded into the right end and an "L" is molded into the left end of each spaced element 28 as a reminder to the technologist to mark x-ray films with right and left correctly.

Contours 24 prevent the backboard and patient from sliding sideways and also facilitate tilting the backboard and patient to prevent aspiration. Once the backboard is tilted, removable angle device 32 (FIG. 1b) is used to support the backboard in at an angle of approximately 60 degrees. Contours 24 also support the backboard when it is tilted at an angle. Angle device 32 may have a triangular shape. Thus, both patient and backboard can be tilted and held in fixed position, if desired. Contour 24 is omitted from center spaced element 28' to avoid a patient's arm being pinched between backboard edge and contour 24 when the backboard is tilted on platform 22.

Platform 22 has indent 34 to store removable angle device 32. Velcro tab 35 facilitates holding angle device 32 in place in indent 34. Indent 34 also firmly holds removable angle device 32 when it is in position to support the backboard and patient. This reliable and stable tilting feature is especially valuable if the patient is heavy or if there is limited staff. Although located under the backboard, a staff member can reach under the backboard in opening 30 to take out removable angle device 32. Alternatively, staff members can tilt the patient and removable angle device 32 can be twisted into position to support the patient.

Troughs 40 within perimeter of platform 22 retain blood dripping down from the backboard, reducing the amount of blood that may go on the stretcher or floor, making the work area safer. Elevated central support area 42 and side supports 44 keep the x-ray cassettes above the blood in troughs 40, keeping the cassettes cleaner. Troughs 40 can also be used to store equipment such as airways or a laryngoscope, which may be stored at head end 45 of platform 22.

Corners 46 of platform 22 are indented, allowing for placement of IV poles (not shown) in the stretcher.

Elevated holes 48 for holding sharps containers (not shown) are also provided on both sides of platform 22 near its ends. Elevating holes 48 prevents blood from entering. Needles and other sharp disposable objects are disposed of directly at the platform, reducing the chance of sticking the patient or another staff member.

Arm boards 56 with double sided Velcro straps (not shown) are used to facilitate controlling a violent or uncooperative patient. Arm board 56 has extension portion 57a that is placed under the upper leg of the patient. The weight of the patient's own body fixes the position of arm board 56 and provides support for the patient's arms on portion 57b. Arm board 56 is secured to the patient's arm and to the backboard with Velcro straps that extend through a slot in the backboard. Arm boards can also be used to stabilize intravenous lines and to keep the patient's arms level with the patient's body as x-ray cassettes are positioned. Platform 22 includes slotted structure 58 for storing arm boards 56 when they are not in use. Arm boards 56 are wide enough where hands would lie to protect fingers of a patient. Arm boards 56 can be used while a patient is on a patient support unit on platform 22 or they may be used while a patient is on a stretcher, a bed, an examining table, or operating table. They are particularly useful for a patient having an intravenous line.

Additional strapping (not shown) could also be wrapped around the patient's upper and lower legs and the backboard to stabilize the position of the patient. Stabilizing to the backboard is faster then providing four-point restraints on the patient and then attaching these restraints to the stretcher. Since the patient is restrained on the backboard, he or she may be safely and confidently moved on the backboard, for example, to a CAT scanner, if necessary.

Figure 2:
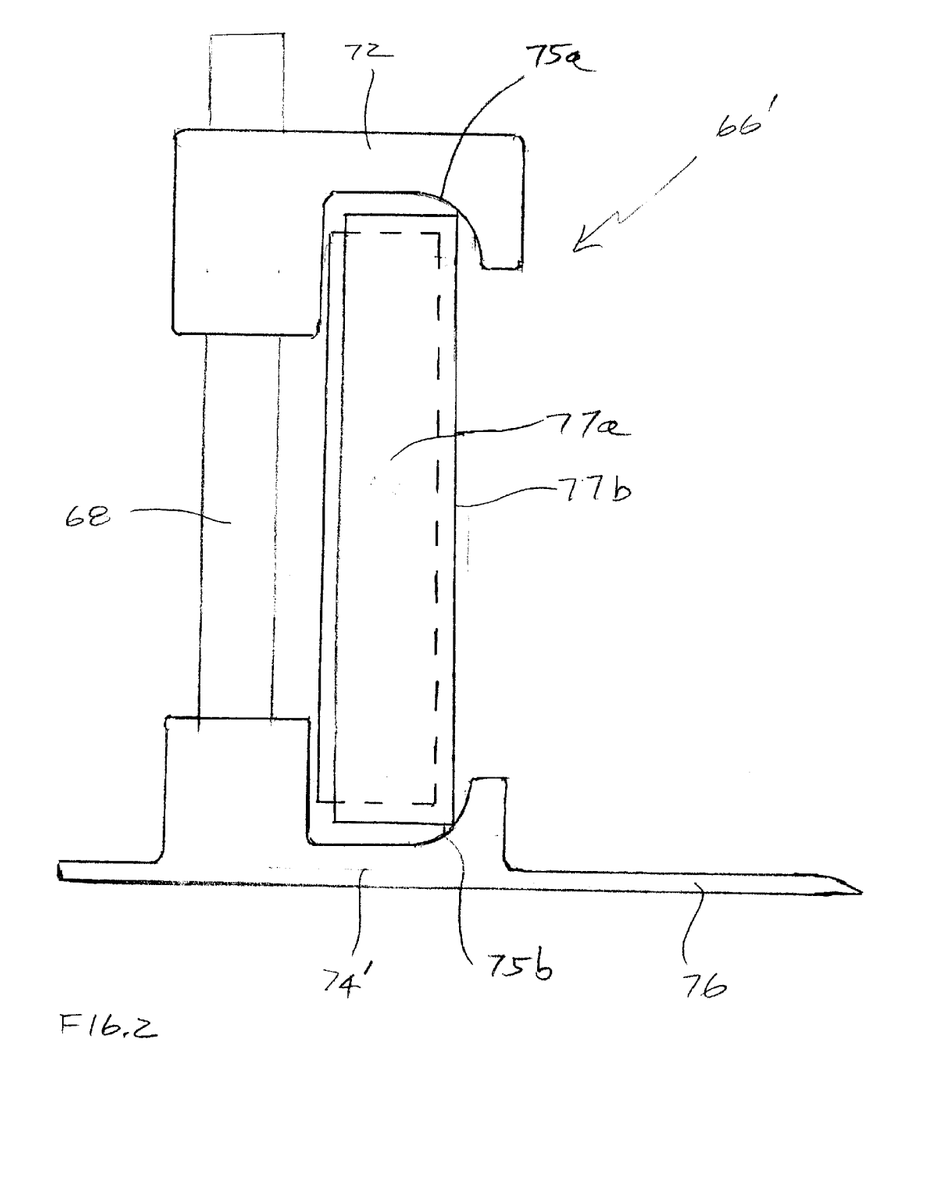
FIG. 2 is a cross sectional view of an x-ray cassette holder of the present invention having a movable upper cassette retainer and a lower cassette retainer integrated with a base.

Swivelling film cassette holder 66, mounted on rod 68, can be mounted in hole 70 in platform 22. Holes 70 can be provided along the perimeter of platform 22 or in spaced elements 28 at various locations as shown in FIG. 1a so a vertical mounted x-ray film cassette can be provided to take any cross-table lateral radiograph of the patient, from head to toe. Cassette holder 66 consists of moveable upper cassette retainer 72 and lower cassette retainer 74 for holding a regular x-ray film cassette (not shown). Lower cassette retainer 74 may be movable, as shown in FIG. 1a or lower cassette retainer 74' may be fixed in position, as shown in FIG. 2. Lower cassette retainer 74' can be integrated with base 76 so cassette holder 66' can be free standing, as shown in FIG. 2 rather than requiring a hole in another unit for support.

A wide cassette or cassette 77a with clip-on grid 77b (or a grid cassette), can be accommodated in cassette holder 66, 66' since at least one of the cassette retainers 72, 74, 74' has curved portion 75a, 75b that accommodates various width cassettes, as shown in FIG. 1a and FIG. 2.

Rod 68 preferably has curved part 78 to provide cassette holder 66 below the level of the backboard. Height of moveable upper cassette retainer 72 is adjustable with knob 79. Similarly, height of lower cassette retainer 74 can also be adjusted.

Cassette holder 66 is also shown in stored position within indent 80 in platform 22.

Small cassette holder 81 (FIG. 1c) can also be placed on the backboard between the patient's legs and used for taking cross-table lateral radiographs of the lower extremities. Small cassette holder 81 includes base unit 82 and swivelling unit 83 that has a pin (not shown) for mounting in hole 84 of base unit 82, as shown in more detail in FIGS. 3a, 3b. Swivelling unit 83 also has slot 85 for holding the cassette vertically. Because slot 85 is sufficiently tall, typically about 2 inches tall, no upper cassette retainer is needed.

Small cassette holder 81 can be stored within indent 89 in platform 22. Swivelling film cassette holder 66 and small cassette holder 81 are held in respective indents in platform 22 with velcro. Large and small cassette holders 72, 74, 74', and 81 and angle device 32 are made of a plastic, such as molded polyurethane.

Platform 22 is rotationally molded of a material such as high density polyethylene (HDPE), a material commonly used for standard backboards that is strong, durable, and easily cleaned and disinfected. Platform 22 is then foam filled. Platform 22 typically has dimensions of 72"×25"×2½". It is substantially wider than a standard 16 inch wide backboard to facilitate collecting body fluids. Platform 22 is about ½ higher under spaced elements 28 to prevent blood from penetrating into a seam between platform 22 and spaced elements 28. Thus, platform 22 is about 8 inches high at spaced elements 28. An appealing color and molded-in graphics enhance its appearance. Arm boards are thermoformed or routed from solid stock of a plastic material, such as ABS or Kydex.

A wall mounting unit (not shown) holds the system while not in use.

Figure 3A:
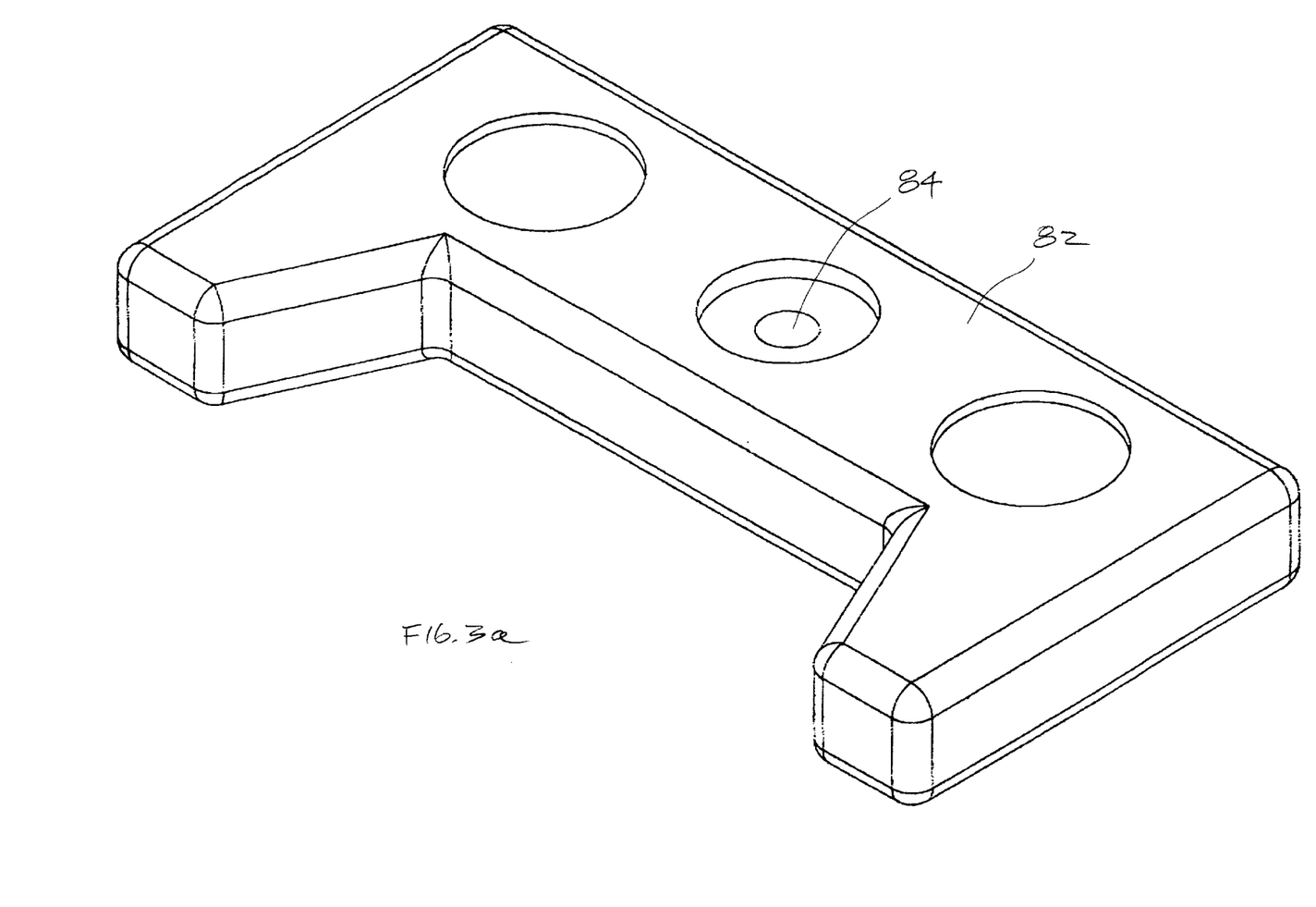
FIG. 3a is a cross sectional view of a base of a small x-ray cassette holder of the present invention.
Figure 3B:
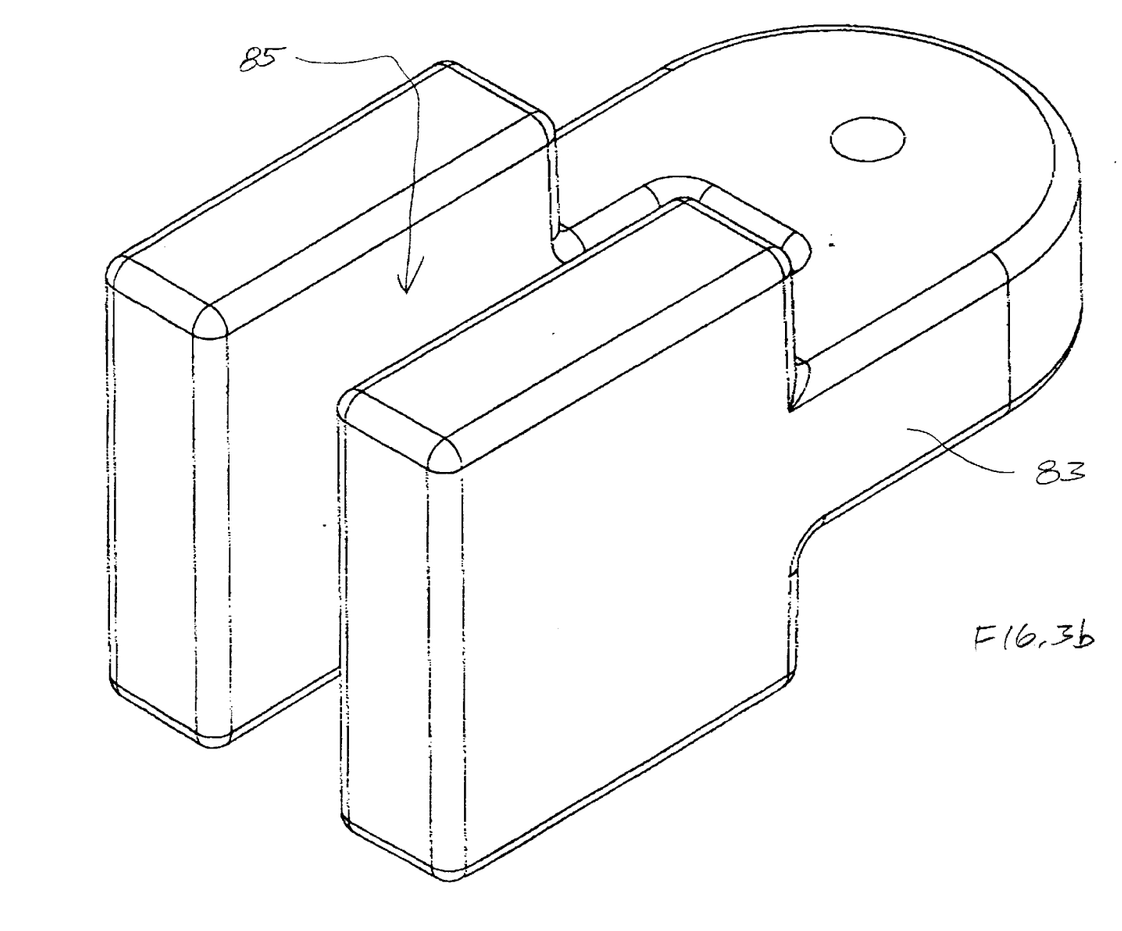
FIG. 3b is a cross sectional view of a slotted swivelling unit of the small x-ray cassette holder of the present invention.
Figure 4A:
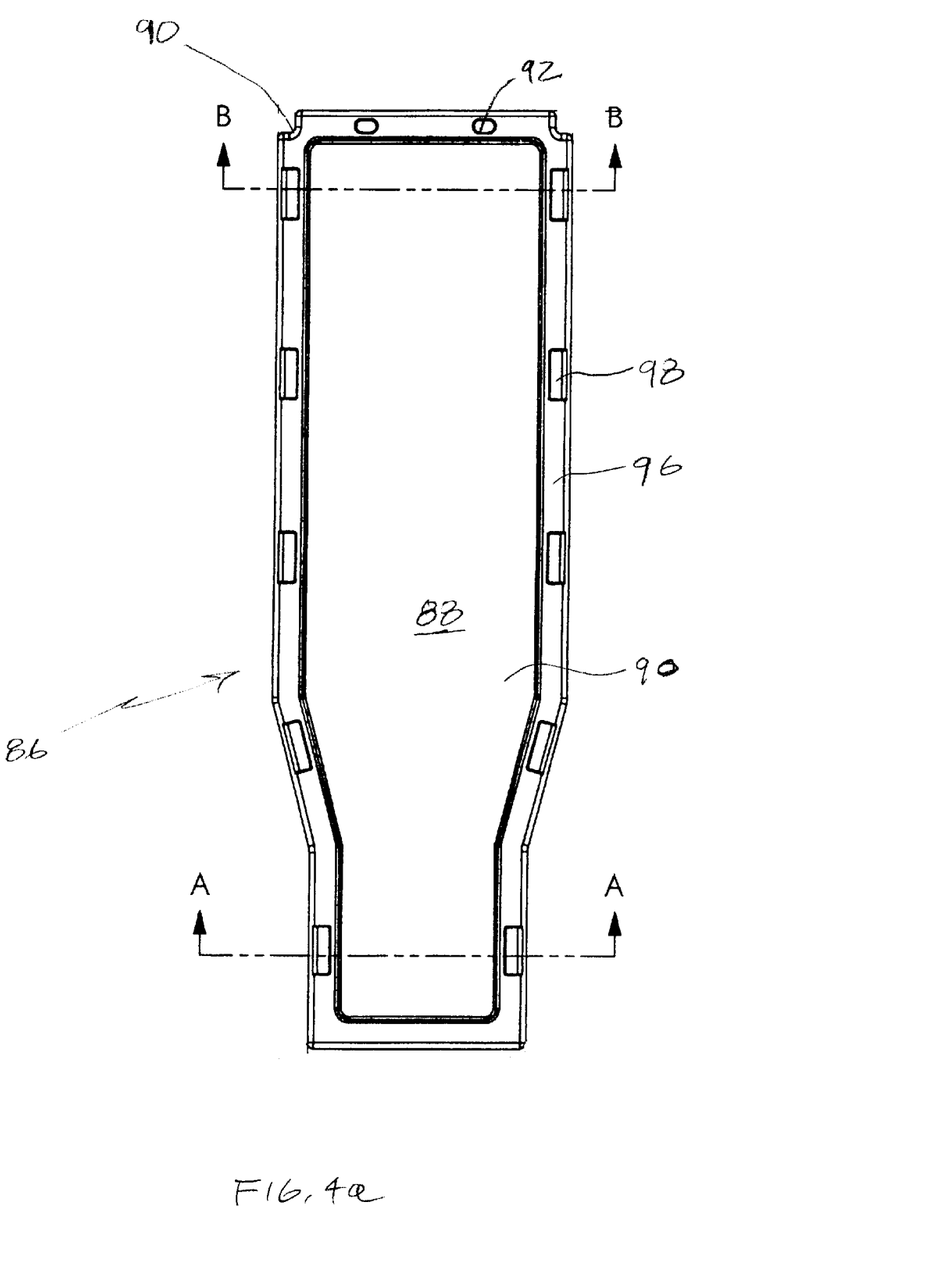
FIG. 4a is a top view of a mattress covered bed of the present invention that can be used as a patent support unit with the platform of FIG. 1.
Figure 4B:
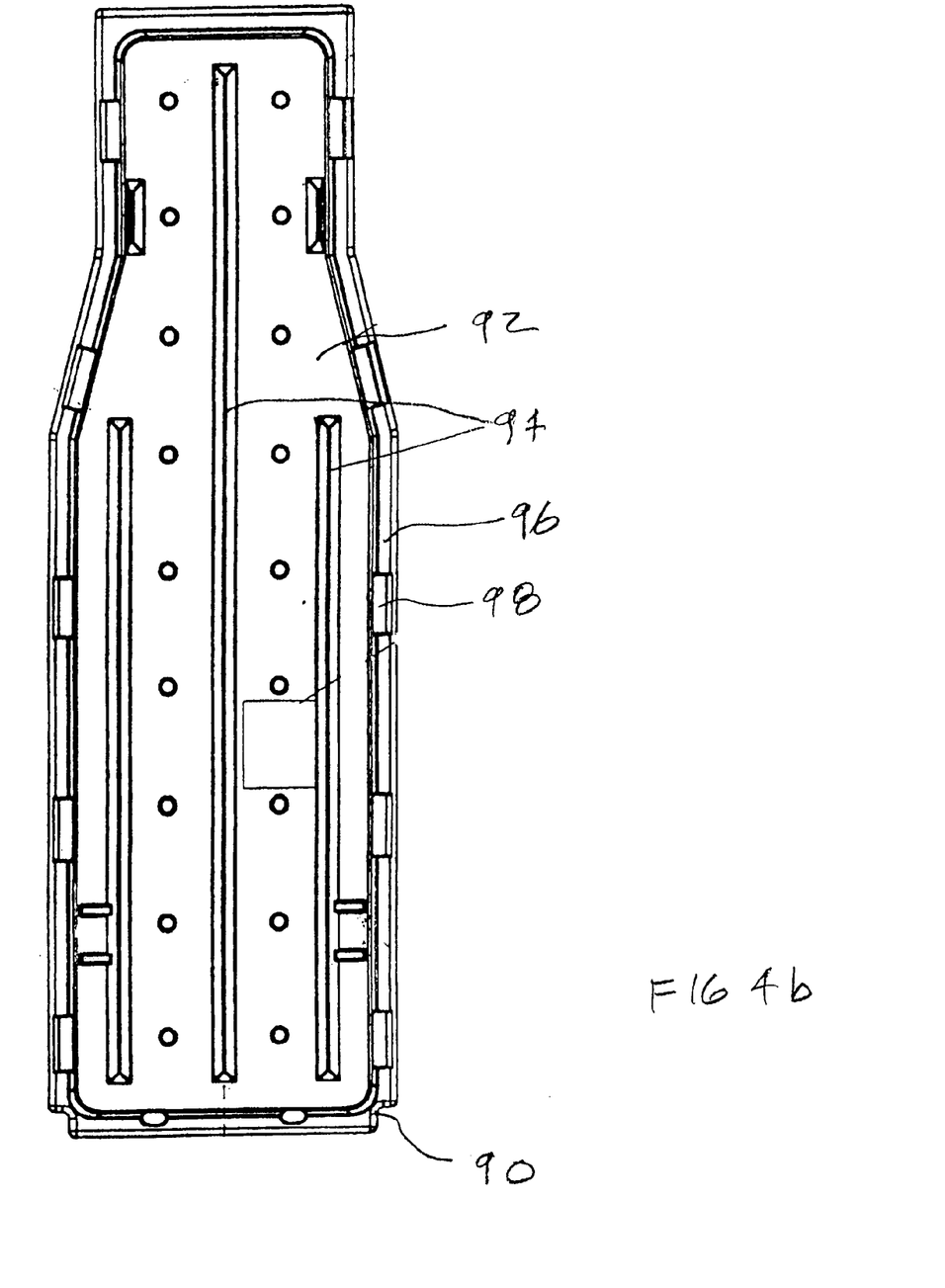
Figure 4D:
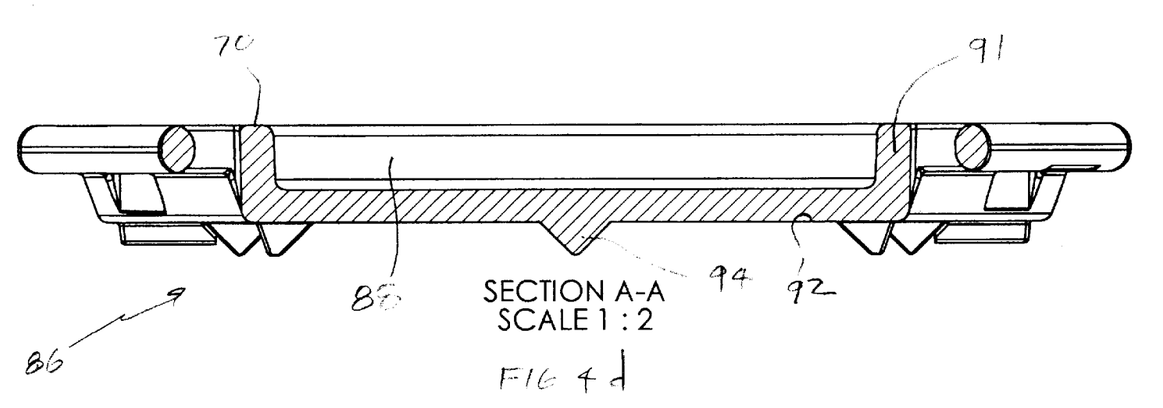
Figure 4E:
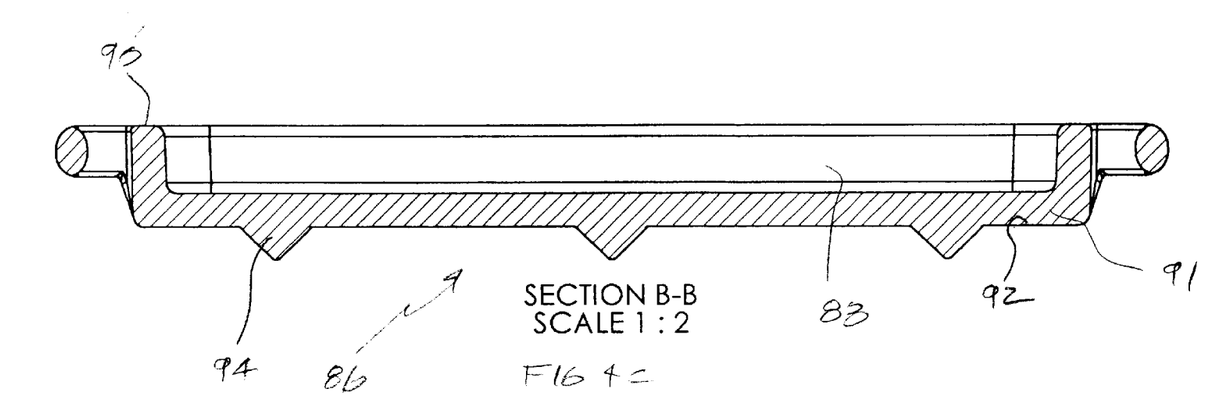

Once examination of the patient shows that a hard surfaced backboard is no longer required, mattress covered bed 86 can be used with platform 22 of the present invention, as shown in FIGS. 3a–3d (the mattress itself is not shown). Preferably, the mattress is located in well 88 in top surface 90 of bed 86. Velcro is also used to retain the mattress within this well. Well 88 restrains the mattress from moving when bed 86 is moved. Preferably the top surface of the mattress is even with top surface 90. Bed 86 includes hard base 91 formed of a plastic material, such as high density polyethylene, as shown in FIGS. 3c, 3d. Lower surface 92 of bed 66 includes runners 94 to increase strength. Bed 86 can be carried, used on a standard stretcher, or used on platform 22. Frame 96 surrounding the mattress has slots 98 to facilitate holding bed 86 with hands during patient transport. Slots 98 can also be used for straps to restrain a patient on bed 86. Straps could extend over a patient or they could just restrain arms and legs. Corners 90 of bed 86 are indented, allowing for placement of IV poles (not shown). Holes 92 are used to support bed 86 on a wall for storage. The movable bed with strap restraints facilitates safely moving a potentially violent patient from one stretcher to another stretcher or to a standard bed.

While several embodiments of the invention, together with modifications thereof, have been described in detail herein and illustrated in the accompanying drawings, it will be evident that various further modifications are possible without departing from the scope of the invention. For example, various additional indents could be provided in platform 22 for other tools. Also, patients can be located on a patient support unit on platform 22 while a treatment, such as surgery, is being performed or while other diagnostic operations, such as CAT scanning, are being performed. Nothing in the above specification is intended to limit the invention more narrowly than the appended claims. The examples given are intended only to be illustrative rather than exclusive.

What is claimed is:

1. A system for supporting a patient, comprising
    a platform having an upper surface, wherein said platform further comprises a trough, wherein said trough is interrupted by an elevated support area for supporting an x-ray cassette above fluid that may collect in said trough;
    a removable patient support unit;
    said platform further comprising spaced elements for supporting said removable patient support unit elevated above said upper surface, wherein said spaced elements are configured for placing said removable patient support unit onto said spaced elements while the patient is on said removable patient support unit; and an unimpeded region between said upper surface and the removable patient support unit when the removable patient support unit is on said spaced elements.

2. The system as recited in claim 1, wherein said platform further comprises a removable x-ray cassette holder extending above said removable patient support unit when said removable patient support unit is on said spaced elements.

3. The system as recited in claim 2, wherein said removable cassette holder comprises a rod.

4. The system as recited in claim 3, wherein said rod fits in a hole in a spaced element or in a hole in said platform.

5. The system as recited in claim 3, wherein said rod can swivel with respect to said platform.

6. The system as recited in claim 3, wherein removable cassette holder further comprises a pair of cassette retainers mounted on said rod.

7. The system as recited in claim 6, wherein position of at least one of said cassette retainers on said rod is adjustable.

8. The system as recited in claim 2, wherein said cassette holder comprises a slot.

9. The system as recited in claim 1, further comprising a device for supporting the patient support unit at an angle.

10. The system as recited in claim 1, wherein said spaced elements are connected to the platform.

11. The system as recited in claim 1, wherein sidewalls of said spaced elements extend at a non-perpendicular angle to said upper surface.

12. The system as recited in claim 1, wherein said spaced elements are contoured.

13. The system as recited in claim 12, wherein contours of said spaced elements match contours of said patient support unit to hold said patient support unit.

14. The system as recited in claim 13 wherein contours of said spaced elements match contours of said patient support unit to hold said patient support unit when it is tilted.

15. The system as recited in claim 1, wherein said platform further comprises a structure for holding a container.

16. The system as recited in claim 15, wherein said structure is a hole.

17. The system as recited in claim 15, wherein the container is for used needles.

18. The system as recited in claim 1, wherein said platform further comprises removable arm boards for supporting a patient's arms.

19. The system as recited in claim 19, wherein said platform further comprises a structure for storing said arm boards on said platform.

20. The system as recited in claim 18, wherein said arm boards are wide enough to protect fingers of a patient.

21. The system as recited in claim 18, wherein said arm boards further comprise a strap to secure a patient's arm to said arm board and to the patient support unit.

22. The system as recited in claim 1, wherein said patient support unit comprises a backboard.

23. The system as recited in claim 1, wherein said patient support comprises at least one hard surface.

24. The system as recited in claim 23, wherein said patient support comprises a bed having a mattress pad.

25. The system as recited in claim 24, wherein said bed has a dimension wider than a backboard.

26. The system as recited in claim 1, wherein said platform and said spaced elements support the patient support unit in a fixed position.

27. The system as recited in claim 1, wherein said platform comprises a part for holding the platform to another structure.

28. The system as recited in claim 27, wherein said other structure comprises a stretcher.

29. The system as recited in claim 27, wherein said part comprises a hole for strapping said platform to said other structure.

30. The system as recited in claim 1, wherein said platform is wider than the removable patient support unit.

31. The system as recited in claim 1, wherein said platform comprises an indent for storing an angle support or a cassette holder.

32. The system as recited in claim 1, wherein said platform comprises raised sections on which said spaced elements are mounted.

33. A system for supporting a patient, comprising
a platform having an upper surface, wherein said platform further comprises a trough, wherein said trough is interrupted by an elevated support area for supporting an x-ray cassette above fluid that may collect in said trough;
said platform further comprising elements for supporting a removable patient support unit elevated above said upper surface; and
an unimpeded region between said upper surface and the removable patient support unit.

34. The system as recited in claim 33, wherein said trough is for retaining bodily fluids or tools.

35. A system for supporting a patient, comprising
a platform having an upper surface;
said platform further comprising spaced elements for supporting a removable patient support unit elevated above said upper surface;
an unimpeded region between said upper surface and the removable patient support unit; and
wherein said platform further comprises a removable x-ray cassette holder extending above said removable patient support unit when said removable patient support unit is on said spaced elements, wherein said removable x-ray cassette holder comprises a rod, wherein said rod has a bend.

36. A system for supporting a patient, comprising
a platform having an upper surface;
said platform further comprising spaced elements for supporting a removable patient support unit elevated above said upper surface, wherein said spaced elements are configured for placing said removable patient support unit onto said spaced elements while the patient is on said removable patient support unit;
an unimpeded region between said upper surface and the removable patient support unit; and
wherein said platform further comprises a removable x-ray cassette holder, wherein said cassette holder comprises a base unit and a slotted swivelling unit for holding a cassette vertically.

37. A system for supporting a patient, comprising
a platform having an upper surface;
said platform further comprising spaced elements for supporting a removable patient support unit elevated above said upper surface, wherein said spaced elements are configured for placing said removable patient support unit onto said spaced elements while the patient is on said removable patient support unit;
an unimpeded region between said upper surface and the removable patient support unit; and a device for supporting the patient support unit at an acute angle with respect to said platform, wherein said device for supporting the patient support comprises a triangular unit.

38. A system for supporting a patient, comprising a platform having an upper surface;

said upper surface having spaced elements for supporting a removable patient support unit elevated above said upper surface;

an unimpeded region between said upper surface and the removable patient support unit; and wherein said removable patient support unit comprises a bed having a mattress pad, wherein said mattress pad is located in a well framed by a hard material.

39. The system as recited in claim 38, wherein said frame of hard material comprises holes.

40. A system for supporting a patient, comprising a platform having spaced elements for supporting a removable patient support unit, wherein said spaced elements are configured for placing said removable patient support unit onto said spaced elements while the patient is on said removable patient support unit, the platform having a plurality of structures for holding a removable x-ray cassette holder wherein one said structure for holding a removable x-ray cassette holder is for holding an x-ray film cassette vertically.

41. The system as recited in claim 40, wherein said platform comprises spaced elements for supporting the patient support unit elevated above said platform.

* * * * *